(12) United States Patent
Park et al.

(10) Patent No.: US 11,923,508 B2
(45) Date of Patent: Mar. 5, 2024

(54) ELECTROLYTE SOLUTION FOR LITHIUM SECONDARY BATTERY AND LITHIUM SECONDARY BATTERY INCLUDING THE SAME

(71) Applicants: SK On Co., Ltd., Seoul (KR); SK Innovation Co., Ltd., Seoul (KR)

(72) Inventors: Ki Sung Park, Daejeon (KR); Myoung Lae Kim, Daejeon (KR)

(73) Assignees: SK On Co., Ltd., Seoul (KR); SK Innovation Co., Ltd., Seoul (KR)

( * ) Notice: Subject to any disclaimer, the term of this patent is extended or adjusted under 35 U.S.C. 154(b) by 0 days.

(21) Appl. No.: 18/349,264

(22) Filed: Jul. 10, 2023

(65) Prior Publication Data
US 2024/0021877 A1    Jan. 18, 2024

(30) Foreign Application Priority Data
Jul. 12, 2022    (KR) ........................ 10-2022-0085429

(51) Int. Cl.
| | |
|---|---|
| *H01M 10/0567* | (2010.01) |
| *C07D 491/044* | (2006.01) |
| *C07F 9/6571* | (2006.01) |
| *H01M 10/052* | (2010.01) |
| *H01M 10/0569* | (2010.01) |

(52) U.S. Cl.
CPC .... *H01M 10/0567* (2013.01); *C07D 491/044* (2013.01); *C07F 9/657163* (2013.01); *H01M 10/052* (2013.01); *H01M 10/0569* (2013.01); *H01M 2300/004* (2013.01)

(58) Field of Classification Search
None
See application file for complete search history.

(56) References Cited

U.S. PATENT DOCUMENTS

| | | |
|---|---|---|
| 2010/0021823 A1 | 1/2010 | Onuki et al. |
| 2013/0004862 A1 | 1/2013 | Miyoshi et al. |
| 2014/0186721 A1 | 7/2014 | Zhang et al. |
| 2019/0305374 A1 | 10/2019 | Tsay et al. |

FOREIGN PATENT DOCUMENTS

| | | | |
|---|---|---|---|
| CN | 110350245 A | * 10/2019 | .......... H01M 10/052 |
| EP | 3604276 A1 | * 2/2020 | |
| KR | 1020180124994 A | 11/2018 | |
| KR | 1020190092284 A | 8/2019 | |
| WO | 2008010665 A1 | 1/2008 | |

OTHER PUBLICATIONS

Machine Translation of CN-110350245-A. (Year: 2019).*

* cited by examiner

*Primary Examiner* — Gregg Cantelmo
(74) *Attorney, Agent, or Firm* — The Webb Law Firm

(57) ABSTRACT

Provided is an electrolyte solution for a lithium secondary battery and a lithium secondary battery including the electrolyte solution. The electrolyte solution includes an additive represented by a specific chemical formula, an organic solvent and a lithium salt. The lithium secondary battery including the electrolyte solution provide enhanced high-temperature properties.

11 Claims, 3 Drawing Sheets

ELECTROLYTE SOLUTION FOR LITHIUM SECONDARY BATTERY AND LITHIUM SECONDARY BATTERY INCLUDING THE SAME

CROSS-REFERENCE TO RELATED APPLICATION

This application claims priority to Korean Patent Application No. 10-2022-0085429 filed Jul. 12, 2022, the disclosure of which is hereby incorporated by reference in its entirety.

BACKGROUND OF THE INVENTION

1. Field of the Invention

The present disclosure relates to an electrolyte solution and a lithium secondary battery comprising the same. More particularly, the present disclosure relates to an electrolyte solution comprising a solvent and an electrolytic salt, and a lithium secondary battery comprising the same.

2. Description of Related Art

A secondary battery which can be charged and discharged repeatedly has been widely employed as a power source of a mobile electronic device such as a camcorder, a mobile phone, a laptop computer, etc.

A lithium secondary battery is actively developed and applied among various types of secondary batteries due to high operational voltage and energy density per unit weight, a high charging rate, a compact dimension, etc.

For example, the lithium secondary battery may include an electrode assembly including a cathode, an anode and a separation layer, and an electrolyte solution immersing the electrode assembly.

A lithium metal oxide may be used as an active material for a cathode of the lithium secondary battery. Examples of the lithium metal oxide include a nickel-based lithium metal oxide.

Surface damages of the nickel-based lithium metal oxide may occur due to repeated charge/discharge cycles to degrade power and capacity, and/or a side reaction may occur between the nickel-based lithium metal oxide and the electrolyte, thereby reducing the service life of the lithium secondary battery.

As use of secondary batteries becomes more popular, the amount of secondary batteries being discarded as waste at the end of their lifespan in increasing. Waste plastics, which are produced using petroleum as a feedstock, are difficult to recycle and are mostly disposed of as garbage. These wastes take a long time to degrade in nature, which causes contamination of the soil and serious environmental pollution. For example, as plastic decomposes by exposure to sunlight and heat, the plastic waste releases greenhouse gases such as methane and ethylene. Incineration of plastic waste releases significant amounts of greenhouse gases (GHG), such as carbon dioxide, nitrous oxide and/or methane, into the environment. Carbon dioxide is the primary greenhouse gas contributing to climate change. Therefore, it is desirable to reduce and/or prevent additional greenhouse gas emissions by increasing the lifespan of secondary batteries to reduce waste and/or ameliorate the release of greenhouse gases into the environment by decomposition and/or incineration of the waste plastic associated with disposal of the secondary batteries. By extending the lifespan of the secondary batteries, environmental pollution and emission of greenhouse gases is reduced. Also, the plastic materials used in the secondary battery may be recycled.

SUMMARY OF THE INVENTION

According to an aspect of the present disclosure, there is provided an electrolyte solution providing improved high-temperature property.

According to an aspect of the present disclosure, there is provided a lithium secondary battery having improved high-temperature property.

In some embodiments, there is provided an electrolyte solution for a lithium secondary battery comprising an additive comprising a compound represented by the following Chemical Formula 1; an organic solvent; and a lithium salt.

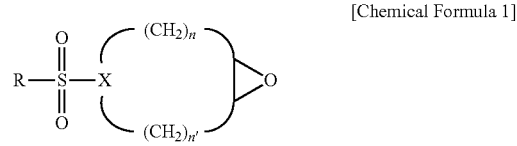

[Chemical Formula 1]

wherein in Chemical Formula 1, R is hydrogen or a substituted or unsubstituted $C_1$-$C_5$ alkyl group, X is N or P, and n and n' are each independently an integer of 1 to 5.

In some embodiments, R may be an unsubstituted $C_1$-$C_3$ alkyl group, and n and n' may each be independently an integer of 1 to 3.

In some embodiments, R may be an unsubstituted $C_1$ alkyl group, X may be N, and n and n' may each be 1.

In some embodiments, the additive may be comprised in an amount ranging from 0.1 wt % to 5 wt % based on a total weight of the electrolyte solution.

In some embodiments, the additive may be comprised in an amount ranging from 0.5 wt % to 2 wt % based on a total weight of the electrolyte solution.

In some embodiments, the organic solvent may comprise at least one selected from the group consisting of a carbonate-based solvent, an ester-based solvent, an ether-based solvent, a ketone-based solvent, an alcohol-based solvent, an aprotic solvent, and mixtures thereof.

In some embodiments, the electrolyte solution may further comprise an auxiliary additive comprising at least one selected from the group consisting of a cyclic carbonate-based compound, a fluorine-substituted carbonate-based compound, a sultone-based compound, a cyclic sulfate-based compound, a phosphate-based compound, and mixtures thereof.

In some embodiments, the auxiliary additive may be comprised in an amount ranging from 0.05 wt % to 20 wt % based on a total weight of the electrolyte solution.

In some embodiments, the auxiliary additive may be comprised in an amount ranging from 0.1 wt % to 15 wt % based on a total weight of the electrolyte solution.

In some embodiments, there is provided a lithium secondary battery comprising an electrode assembly in which a plurality of cathodes and a plurality of anodes are repeatedly stacked, a case accommodating the electrode assembly, and the electrolyte solution for a lithium secondary battery according to any of the embodiments disclosed herein accommodated together with the electrode assembly in the case.

In some embodiments, there is provided an electrolyte solution comprising an additive in an electrolyte solution for a lithium secondary battery that may form a robust solid electrolyte interphase (SEI) on an electrode surface.

Accordingly, a lithium secondary battery having improved high-temperature storage properties (e.g., a capacity retention and/or prevention of resistance/thickness increase of the battery under high-temperature conditions) can be implemented.

The electrolyte solution for a lithium secondary battery as disclosed herein may provide a lithium secondary battery having improved high-temperature stability (e.g., suppression of gas generation in a high-temperature environment).

BRIEF DESCRIPTION OF THE DRAWINGS

These and other features and characteristics of the present disclosure, as well as the functions of the related elements of structures and the combination of components and economies of manufacture, will become more apparent upon consideration of the disclosure herein with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which.

DESCRIPTION OF THE INVENTION

Figure 1:
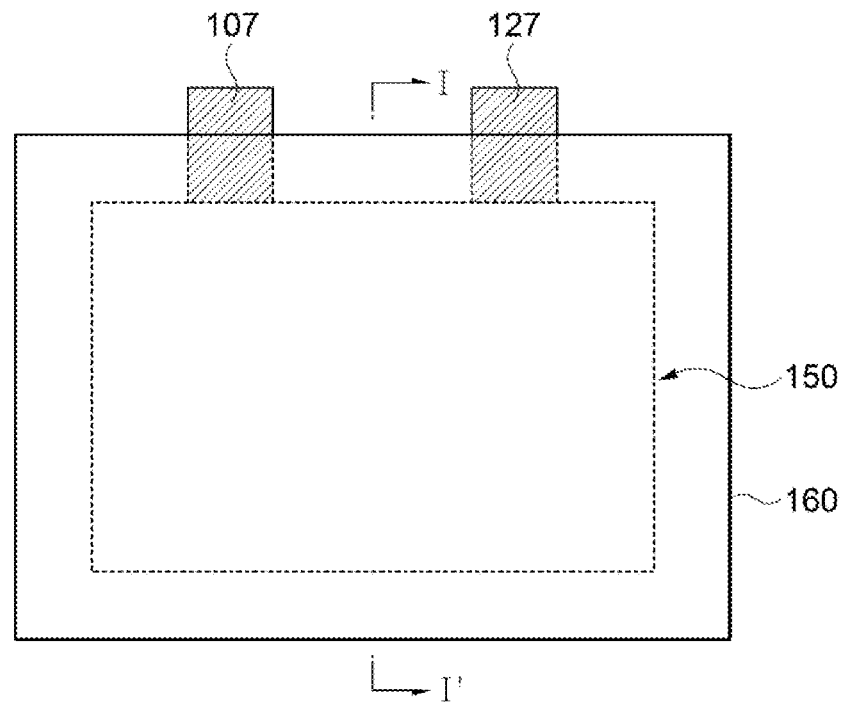
FIG. 1 is a schematic plan view illustrating a lithium secondary battery in accordance with example embodiments.

According to embodiments of the present invention, there is provided an electrolyte solution which comprises an additive having a predetermined chemical structure disclosed herein. Also, there is provided a lithium secondary battery comprising the electrolyte solution.

Throughout the specification, unless explicitly described to the contrary, "comprising", "including" or "containing" any constituent elements will be understood to imply further inclusion of other constituent elements.

Unless the context clearly indicates otherwise, the singular forms of the terms used in the present specification may be interpreted as including the plural forms. As used herein, the singular form of "a", "an", and "the" include plural referents unless the context clearly states otherwise.

For the purposes of this specification, unless otherwise indicated, all numbers expressing quantities of ingredients, reaction conditions, dimensions, physical characteristics, and so forth used in the specification and claims are to be understood as being modified in all instances by the term "about." Hereinafter, unless otherwise defined herein, "about" may be considered as a value within 30%, 25%, 20%, 15%, 10%, 5%, 3%, 2%, 1%, 0.5%, 0.1%, 0.05% or 0.01 of the specified value. Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

In the present specification, the term "A-based compound" may refer to a compound comprising a group A and/or a derivative of the compound.

In the present specification, the term "Ca-Cb" refers that the number of carbon (C) atoms is from a to b.

<Electrolyte Solution for Lithium Secondary Battery>

In some embodiments, there is provided an electrolyte solution for a lithium secondary battery comprising an additive comprising a compound represented by Chemical Formula 1, an organic solvent and a lithium salt. A lithium secondary battery comprising the electrolyte solution may provide improved high-temperature stability and storage properties.

Hereinafter, components of the electrolyte solution for a lithium secondary battery will be described in detail.

Additive

The electrolyte solution for a lithium secondary battery according to some embodiments may comprise an additive comprising a compound represented by Chemical Formula 1

[Chemical Formula 1]

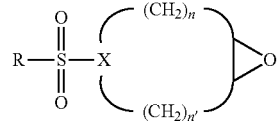

wherein in Chemical Formula 1, R may be hydrogen or a substituted or unsubstituted $C_1$-$C_5$ alkyl group, X is N or P, and n and n' are each independently an integer from 1 to 5.

For example, R may be hydrogen or a substituted or unsubstituted $C_1$-$C_5$ alkyl group. In some embodiments, $R^2$ may be an unsubstituted $C_1$-$C_3$ alkyl group, e.g., an unsubstituted $C_1$ alkyl group (a methyl group).

For example, X may be N or P. N represents nitrogen and P represents phosphorus.

In some embodiments, X may be N.

For example, n and n' in Chemical Formula 1 may each independently be an integer of 1 to 5. In some embodiments, n and n' may each be from 1 to 3, e.g., may be 1.

For example, n and n' in Chemical Formula 1 may be the same as or different from each other. In some embodiments, n and n' may be the same as each other.

For example, the alkyl group may mean a portion in a molecule composed of carbon and hydrogen. The alkyl group may mean a partial remaining structure assuming that one hydrogen atom is removed from the alkane ($C_nH_{2n+2}$). For example, $CH_3$— indicates a methyl group, and $CH_3$—$CH_2$—$CH_2$— indicates a propyl group.

For example, the term "substituted" used herein refers that a substituent may be further bonded to a carbon atom of the alkyl group or the alkylene group by substituting a hydrogen atom of the alkyl group or the alkylene group with the substituent. For example, the substituent may be at least one of a halogen, a $C_1$-$C_6$ alkyl group, a $C_2$-$C_6$ alkenyl group, an amino group, a $C_1$-$C_6$ alkoxy group, a $C_3$-$C_7$ cycloalkyl group, or a 5 to 7-membered hetero-cycloalkyl group. In some embodiments, the substituent may be a halogen or a $C_1$-$C_6$ alkyl group.

The additive comprising the compound represented by Chemical Formula 1 may be comprised in the electrolyte solution for a secondary battery, so that a robust solid electrolyte interphase (SEI) layer may be formed on an electrode through a ring-opening reductive decomposition reaction of a cyclic structure.

For example, the solid electrolyte interphase layer based on a sulfonate functional group may be formed under a high temperature condition. Accordingly, decomposition of an organic solvent (e.g., EC, EMC, etc.) may be effectively prevented, and gas generation and battery thickness increase may be significantly reduced.

In some embodiments, the compound represented by Chemical Formula 1 may comprise 3-(methylsulfonyl)-6-oxa-3-azabicyclo[3.1.0]hexane. 3-(methylsulfonyl)-6-oxa-3-azabicyclo[3.1.0]hexane may be represented by Chemical Formula 1-1.

[Chemical Formula 1-1]

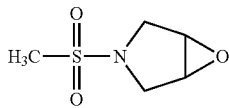

The compound represented by Chemical Formula 1 may be comprised as the additive of the electrolyte solution for a secondary battery, so that a stable SEI layer may be formed on the electrode (anode) by the ring-opening reductive decomposition reaction of the cyclic structure. Accordingly, improved capacity retention may be obtained, and increase of a battery resistance and a battery thickness may be prevented in high-temperature conditions.

In some embodiments, a content of the additive content may be adjusted to be 0.1 weight percent (wt %) or more, 0.2 wt % or more, 0.3 wt % or more, 0.4 wt % or more, 0.5 wt % or more, or 1 wt % or more based on a total weight of the electrolyte solution in consideration of sufficient passivation and stable SEI film formation.

In some embodiments, the content of the additive may be adjusted to be 10 wt % or less, 9 wt % or less, 7 wt % or less, 6 wt % or less, 5 wt % or less, 4.5 wt % or less, 4 wt % or less, 3.5 wt % or less, 3 wt % or less, or 2 wt % or less based on the total weight of the electrolyte solution in consideration of lithium ion mobility and active material activity in the electrolyte solution.

In some embodiments, the content of the additive may be in a range from 0.1 wt % wt % to 5 wt %, or from 0.5 wt % to 2 wt %. Within the above range, the above-described anode passivation may be sufficiently implemented while preventing an excessive degradation of lithium ion mobility and activity of a cathode active material. Further, increase of the battery resistance and the battery thickness may be prevented while enhancing capacity retention under the high-temperature conditions.

Auxiliary Additive

The electrolyte solution for a rechargeable lithium battery may further comprise an auxiliary additive together with the above-described additive.

The auxiliary additive may comprise, e.g., a cyclic carbonate-based compound, a fluorine-substituted carbonate-based compound, a sultone-based compound, a cyclic sulfate-based compound and/or a phosphate-based compound.

In some embodiments, a content of the auxiliary additive may be adjusted to be 10 wt % or less, 9 wt % or less, 8 wt % or less, 7 wt % or less, 6 wt % or less, 5 wt % or less, 4 wt % or less, 3 wt % or less, 2 wt % or less, or 1 wt % or less based on the total weight of the electrolyte solution in consideration of an interaction with the additive comprising the compound represented by Chemical Formula 1

In some embodiments, the content of the auxiliary additive may be adjusted to be 0.01 wt % or more, 0.02 wt % or more, 0.03 wt % or more, 0.05 wt % or more, 0.1 wt % or more, 0.2 wt % or more, 0.3 wt % or more, 0.4 wt % or more, or 0.5 wt % or more in consideration of the SEI film stabilization.

In some embodiments, the auxiliary additive may be comprised in an amount from 0.05 wt % to 20 wt %, from 0.1 wt % to 15 wt %, or from 0.1 wt % to 10 wt % based on the total weight of the electrolyte solution. Within the above range, durability of the protective film may be enhanced and high-temperature storage properties may be improved without degrading the function of the main additive.

The cyclic carbonate-based compound may comprise vinylene carbonate (VC), and/or vinyl ethylene carbonate (VEC), etc.

The fluorine-substituted cyclic carbonate-based compound may comprise fluoroethylene carbonate (FEC).

The sultone-based compound may comprise 1,3-propane sultone, 1,3-propene sultone, and/or 1,4-butane sultone. etc.

The cyclic sulfate-based compound may comprise 1,2-ethylene sulfate, and/or 1,2-propylene sulfate, etc.

The phosphate-based compound may comprise an oxalatophosphate-based compound such as lithium bis(oxalato)phosphate.

In some embodiments, the fluorine-substituted cyclic carbonate-based compound, the sultone-based compound, the cyclic sulfate-based compound and the oxalatophosphate-based compound may be used together as the auxiliary additive.

Durability and stability of the electrode may be further improved by the addition of the auxiliary additive. The auxiliary additive may be comprised in an appropriate amount within a range that does not inhibit the lithium ion mobility in the electrolyte solution.

Organic Solvent and Lithium Salt

The organic solvent may comprise an organic compound that provides sufficient solubility for the lithium salt, the additive and the auxiliary additive and may have no substantial reactivity in the battery.

For example, the organic solvent may comprise a carbonate-based solvent, an ester-based solvent, an ether-based solvent, a ketone-based solvent, an alcohol-based solvent, an aprotic solvent, etc. These may be used alone or in a combination thereof.

In some embodiments, the organic solvent may comprise a carbonate-based solvent. The carbonate-based solvent may comprise a linear carbonate-based solvent and a cyclic carbonate-based solvent.

For example, the linear carbonate-based solvent may comprise at least one of dimethyl carbonate (DMC), ethyl methyl carbonate (EMC), diethyl carbonate (DEC), methyl propyl carbonate, ethyl propyl carbonate and/or dipropyl carbonate.

For example, the cyclic carbonate-based solvent may comprise at least one of ethylene carbonate (EC), propylene carbonate (PC) and/or butylene carbonate.

In some embodiments, in the organic solvent, an amount of the linear carbonate-based solvent may be greater than an amount of the cyclic carbonate-based solvent on a volume basis.

For example, a mixed volume ratio of the linear carbonate-based solvent and the cyclic carbonate-based solvent may be from 1:1 to 9:1 or from 1.5:1 to 4:1 in some embodiments.

For example, the ester-based solvent may comprise at least one of methyl acetate (MA), ethyl acetate (EA), n-propyl acetate (n-PA), 1,1-dimethylethyl acetate (DMEA), methyl propionate (MP) and/or ethyl propionate (EP).

For example, the ether-based solvent may comprise at least one of dibutyl ether, tetraethylene glycol dimethyl ether (TEGDME), diethylene glycol dimethyl ether (DEGDME), dimethoxyethane, tetrahydrofuran (THF) and/or 2-methyltetrahydrofuran.

For example, the ketone-based solvent may comprise cyclohexanone. The alcohol-based solvent may comprise, e.g., at least one of ethyl alcohol and/or isopropyl alcohol.

For example, the aprotic solvent may comprise at least one of a nitrile-based solvent, an amide-based solvent (e.g., dimethylformamide), a dioxolane-based solvent (e.g., 1,3-dioxolane), and/or a sulfolane-based solvent, etc. These may be used alone or in a combination thereof.

The electrolyte may comprise, e.g., a lithium salt. For example, the lithium salt may be expressed as $Li^+X^-$. Non-limiting examples of the anion $X^-$ may comprise any one selected from $F^-$, $Cl^-$, $Br^-$, $I^-$, $NO_3^-$, $N(CN)_2^-$, $BF_4^-$, $C_1O_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, or $(CF_3CF_2SO_2)_2N^-$, etc.

In some embodiments, the lithium salt may comprise at least one of $LiBF_4$ and/or $LiPF_6$.

In an embodiment, the lithium salt may be comprised in a concentration from 0.01 M to 5M, or from 0.01 M to 2M with respect to the organic solvent. Within the above range, transfer of lithium ions and/or electrons may be promoted during charging and discharging of the lithium secondary battery.

<Lithium Secondary Battery>

Figure 2:
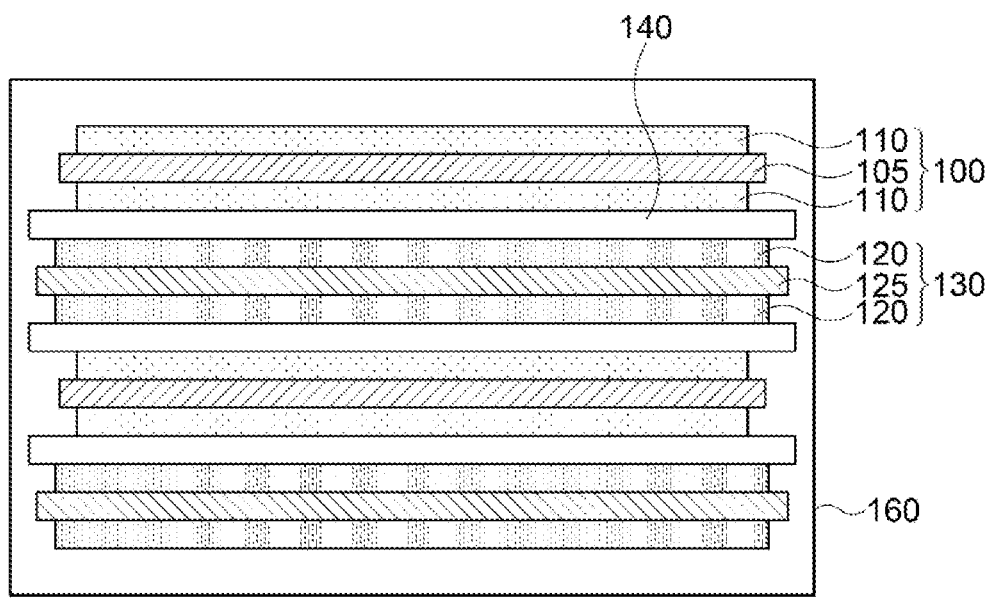
FIG. 2 is a schematic cross-sectional view illustrating a lithium secondary battery in accordance with example embodiments.

FIGS. 1 and 2 are a schematic plan view and a schematic cross-sectional view, respectively, illustrating a lithium secondary battery in accordance with exemplary embodiments. FIG. 2 is cross-sectional view taken along a line I-I' of FIG. 1.

Referring to FIGS. 1 and 2, a lithium secondary battery may comprise an electrode assembly comprising a cathode 100 and an anode 130 facing the cathode 100.

The cathode 100 may comprise a cathode current collector 105 and a cathode active material layer 110 on the cathode current collector 105. The cathode active material layer 110 may comprise a cathode active material. The cathode active material layer 110 may further comprise a cathode binder and a conductive material.

For example, a cathode slurry may be prepared by mixing and stirring the cathode active material, the cathode binder, the conductive material, a dispersive medium, etc., and then the cathode slurry may be coated on the cathode current collector 105, dried and pressed to form the cathode 100.

For example, the cathode current collector 105 may comprise stainless steel, nickel, aluminum, titanium, copper, and/or an alloy thereof.

The cathode active material may comprise lithium metal oxide particles capable of reversibly intercalating and de-intercalating lithium ions. In an embodiment, the cathode active material may comprise the lithium metal oxide particles containing nickel.

In some embodiments, the lithium metal oxide particle may comprise 80 mol % or more of nickel based on a total number of moles of all elements except lithium and oxygen. In this case, the lithium secondary battery having a high capacity may be implemented.

In some embodiments, the lithium metal oxide particle may comprise 83 mol % or more, 85 mol % or more, 90 mol % or more, or 95 mol % or more of nickel based on the total number of moles of all elements except lithium and oxygen.

In some embodiments, the lithium metal oxide particle may further comprise at least one of cobalt and/or manganese.

In some embodiments, the lithium metal oxide particle may further comprise cobalt and manganese. In this case, the lithium secondary battery having enhanced power and penetration stability may be implemented.

In some embodiments, the lithium metal oxide particle may be represented by Chemical Formula 2 below.

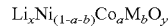

$$Li_xNi_{(1-a-b)}Co_aM_bO_y \quad \text{[Chemical Formula 2]}$$

In some embodiments, in Chemical Formula 2, M may comprise at least one of Al, Zr, Ti, Cr, B, Mg, Mn, Ba, Si, Y, W and/or Sr, $0.9 \le x \le 1.2$, $1.9 \le y \le 2.1$, and $0 \le a+b \le 0.5$.

In some embodiments, $0 < a+b \le 0.4$, $0 < a+b \le 0.3$, $0 < a+b \le 0.2$, $0 < a+b \le 0.17$, $0 < a+b \le 0.15$, $0 < a+b \le 0.12$, and $0 < a+b \le 0.1$.

In some embodiments, the lithium metal oxide particles may further comprise a coating element or a doping element. In some embodiments, the coating element or doping element may comprise Al, Ti, Ba, Zr, Si, B, Mg, P, Sr, W, La, an alloy thereof, and/or an oxide thereof. In this case, the lithium secondary battery having improved life-span properties may be implemented.

In some embodiments, the cathode binder may comprise an organic based binder such as polyvinylidenefluoride (PVDF), a polyvinylidene fluoride-hexafluoropropylene copolymer (PVDF-co-HFP), polyacrylonitrile, and/or polymethylmethacrylate, etc., or an aqueous based binder such as styrene-butadiene rubber (SBR) that may be used with a thickener such as carboxymethyl cellulose (CMC).

In some embodiments, the conductive material may comprise a carbon-based material such as graphite, carbon black, graphene, and/or carbon nanotube, etc., a metal-based material such as tin, tin oxide, titanium oxide, and/or a perovskite material such as $LaSrCoO_3$ and/or $LaSrMnO_3$, etc.

In some embodiments, the anode 130 may comprise an anode current collector 125 and an anode active material layer 120 on the anode current collector 125. The anode active material layer 120 may comprise an anode active material, and may further comprise an anode binder and a conductive material.

In some embodiments, the anode active material may be mixed and stirred together with a binder and conductive material, etc., in a solvent to form an anode slurry. The anode slurry may be coated on the anode current collector 125, dried and pressed to obtain the anode 130.

In some embodiments, the anode current collector 125 may comprise gold, stainless steel, nickel, aluminum, titanium, copper, and/or an alloy thereof. In some embodiments, the anode current collector 125 may comprise copper or a copper alloy.

In some embodiments, the anode active material may be a material capable of intercalating and de-intercalating lithium ions. For example, the anode active material may comprise a lithium alloy, a carbon-based material, and/or a silicon-based material, etc.

In some embodiments, the lithium alloy may comprise a metal element such as aluminum, zinc, bismuth, cadmium, antimony, silicon, lead, tin, gallium, and/or indium, etc.

In some embodiments, the carbon-based material may comprise a crystalline carbon, an amorphous carbon, a carbon composite, and/or a carbon fiber, etc.

In some embodiments, the amorphous carbon may comprise hard carbon, coke, a mesocarbon microbead (MCMB) calcined at 1500° C. or less, a mesophase pitch-based carbon fiber (MPCF), etc. The crystalline carbon may comprise, e.g., natural graphite, graphitized coke, graphitized MCMB, and/or graphitized MPCF, etc.

In some embodiments, the anode active material may comprise the silicon-based material. For example, the silicon-based material may comprise Si, SiOx (0<x<2), Si/C, SiO/C, and/or a Si-Metal, etc. In this case, a lithium secondary battery having a high capacity may be implemented.

For example, when the anode active material comprises the silicon-based material, the battery thickness may be increased during repeated charging and discharging. The lithium secondary battery according to embodiments of the present disclosure may comprise the above-described electrolyte solution, so that the increase of the battery thickness may be reduced or suppressed.

In some embodiments, a content of the silicon-based active material in the anode active material may be in a range from 1 wt % to 20 wt %, 1 wt % to 15 wt %, or 1 wt % to 10 wt %.

In some embodiments, the anode binder and the conductive material may comprise materials substantially the same as or similar the above-described cathode binder and conductive material. In some embodiments, the anode binder may comprise the aqueous binder such as styrene-butadiene rubber (SBR) that may be used together with a thickener such as carboxymethyl cellulose (CMC).

In some embodiments, a separation layer 140 may be interposed between the cathode 100 and the anode 130.

In some embodiments, an area of the anode 130 may be greater than an area of the cathode 100. In this case, lithium ions generated from the cathode 100 may be easily transferred to the anode 130 without being precipitated.

In some embodiments, the separation layer 140 may comprise a porous polymer film prepared from, e.g., a polyolefin-based polymer such as an ethylene homopolymer, a propylene homopolymer, an ethylene/butene copolymer, an ethylene/hexene copolymer, an ethylene/methacrylate copolymer, and/or the like. In some embodiments, the separation layer 140 may also comprise a non-woven fabric formed from a glass fiber with a high melting point, a polyethylene terephthalate fiber, and/or the like.

In some embodiments, an electrode cell may be defined by the cathode 100, the anode 130 and the separation layer 140, and a plurality of the electrode cells may be stacked to form an electrode assembly 150. In some embodiments, the electrode assembly 150 may be formed by winding, laminating or z-folding of the separation layer 140.

The lithium secondary battery according to some embodiments may comprise a cathode lead 107 connected to the cathode 100 to protrude to an outside of a case 160, and an anode lead 127 connected to the anode 130 to protrude to the outside of the case 160.

In some embodiments, the cathode lead 107 may be electrically connected to the cathode current collector 105. The anode lead 127 may be electrically connected to the anode current collector 125.

In some embodiments, the cathode current collector 105 may comprise a protrusion (a cathode tab, not illustrated) at one side thereof. The cathode active material layer 110 may not be formed on the cathode tab. The cathode tab 106 may be integral with the cathode current collector 105 or may be connected to the cathode current collector 105 by, e.g., welding. The cathode current collector 105 and the cathode lead 107 may be electrically connected via the cathode tab.

In some embodiments, the anode current collector 125 may comprise a protrusion (an anode tab, not illustrated) at one side thereof. The anode active material layer 120 may not be formed on the anode tab. The anode tab 126 may be integral with the anode current collector 125 or may be connected to the anode current collector 125 by, e.g., welding. The anode electrode current collector 125 and the anode lead 127 may be electrically connected via the anode tab.

In some embodiments, the electrode assembly 150 may comprise a plurality of the cathodes and a plurality of the anodes. In some embodiments, the cathodes and the anodes may be alternately disposed, and the separation layer may be interposed between the cathode and the anode. Each of the plurality of the cathodes may comprise the cathode tab. Each of the plurality of the anodes may comprise the anode tab.

In some embodiments, the cathode tabs (or the anode tabs) may be laminated, pressed and welded to form a cathode tab stack (or an anode tab stack). The cathode tab stack may be electrically connected to the cathode lead 107. The anode tab stack may be electrically connected to the anode lead 127.

In some embodiments, the electrode assembly 150 may be accommodated together with the electrolyte solution according to the above-described embodiments in a case 160 to form the lithium secondary battery.

In some embodiments, the lithium secondary battery may be fabricated into a cylindrical shape using a can, a prismatic shape, a pouch shape, a coin shape, etc.

A method is provided for reducing greenhouse gas emissions, comprising: preparing a lithium secondary battery, comprising: an electrode assembly in which a plurality of cathodes and a plurality of anodes are repeatedly stacked; a case accommodating the electrode assembly; and an electrolyte solution for a lithium secondary battery, comprising: an additive comprising a compound represented by Chemical Formula 1; an organic solvent; and a lithium salt:

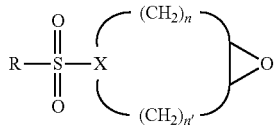

[Chemical Formula 1]

wherein, in Chemical Formula 1, R is hydrogen or a substituted or unsubstituted $C_1$-$C_5$ alkyl group, X is N or P, and n and n' are each independently an integer of 1 to 5, accommodated together with the electrode assembly in the case.

A method is provided for reducing environmental pollution from a lithium secondary battery, comprising: preparing a lithium secondary battery, comprising: an electrode assembly in which a plurality of cathodes and a plurality of anodes are repeatedly stacked; a case accommodating the electrode assembly; and an electrolyte solution for a lithium secondary battery, comprising: an additive comprising a compound represented by Chemical Formula 1; an organic solvent; and a lithium salt:

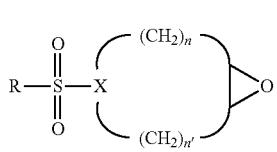

[Chemical Formula 1]

wherein, in Chemical Formula 1, R is hydrogen or a substituted or unsubstituted $C_1$-$C_5$ alkyl group, X is N or P, and n and n' are each independently an integer of 1 to 5, accommodated together with the electrode assembly in the case.

Hereinafter, specific examples and comparative examples are proposed to more concretely describe the present invention. However, the following examples are only given for illustrating the present invention and those skilled in the related art will obviously understand that various alterations and modifications are possible within the scope and spirit of the present invention.

EXAMPLES AND COMPARATIVE EXAMPLES (1) Synthesis Example of 3-(methylsulfonyl)-6-oxa-3-azabicyclo[3.1.0]hexane 1) Methane sulfonamide (2.0 g, 21.0 mmol), potassium carbonate (14.5 g, 105.0 mmol) and 100 ml of acetonitrile were added to a rounded bottom flask, and the stirred. 1,4-dichloro-2-butene (2.56 ml, 23.1 mmol) was slowly added to the reaction solution and stirred for 12 hours. The obtained solid product was filtered and washed with ethyl acetate. A solvent was removed from the filtrate under reduced pressure and dried to obtain 1.0 g of 1-(methylsulfonyl)-1H-pyrrole as a white solid as an intermediate (yield: 32%).

$^1$H-NMR (500 MHz, CDCl$_3$): 5.82 (2H, s), 4.20 (4H, s), 2.85 (3H, s)

2) The above-obtained intermediate (1.0 g, 6.8 mmol) and 40 ml of dichloromethane were added to a rounded bottom flask to prepare a reaction solution, followed by stirring. Meta-chloroperoxybenzoic acid (3.05 g, 13.6 mmol) was added slowly to the reaction solution. Thereafter, the mixture was reacted by stirring for 12 hours.

The product was washed with a saturated aqueous solution of sodium hydrogen carbonate and distilled water. Thereafter, a solvent was removed under reduced pressure and purified by a silica gel column chromatography to obtain 0.9 g of 3-(methylsulfonyl)-6-oxa-3-azabicyclo[3.1.0]hexane as a white solid sample (yield: 81%).

$^1$H-NMR (500 MHz, CDCl$_3$): 3.73 (4H, t), 3.47 (2H, d), 2.80 (3H, s)

(2) Preparation of Electrolyte Solution

A 1.0 M LiPF$_6$ solution (EC/EMC/DEC mixed solvent in a 25:45:30 volume ratio) was prepared.

In the LiPF$_6$ solution, the additive and auxiliary additives were added and mixed with contents (wt %) shown in Table 1 below based on a total weight of an electrolyte solution to form electrolyte solutions of Examples and Comparative Examples.

(5) Fabrication of Lithium Secondary Battery Sample

Li[Ni$_{0.8}$Co$_{0.1}$Mn$_{0.1}$]O$_2$, carbon black and polyvinylidene fluoride (PVDF) were dispersed in N-methyl pyrrolidone (NMP) in a weight ratio of 98:1:1 to prepare a cathode slurry.

The cathode slurry was uniformly coated on a region of an aluminum foil having a protrusion (cathode tab) except for the protrusion, and dried and pressed to prepare a cathode.

Anode active material comprising graphite and SiOx (0<x<2) in a weight ratio of 91:6, styrene-butadiene rubber (SBR) and carboxymethyl cellulose (CMC) were dispersed in water by a weight ratio of 97:0.1:2.9 to form an anode slurry.

The anode slurry was uniformly coated on a region of a copper foil having a protrusion (anode tab) except for the protrusion, and dried and pressed to prepare an anode.

An electrode assembly was formed by interposing a polyethylene separator between the cathode and the anode. A cathode lead and an anode lead were connected to the cathode tab and the anode tab, respectively, by welding.

The electrode assembly was accommodated in a pouch (case) so that partial regions of the cathode lead and the anode lead were exposed to an outside, and three sides except for an electrolyte injection side were sealed.

A lithium secondary battery sample was prepared by injecting the electrolyte solution prepared in the above (1), sealing the electrolyte injection side, and then impregnating for 12 hours.

TABLE 1

| | | auxiliary additive (wt %) | | | |
| --- | --- | --- | --- | --- | --- |
| | additive | LiPO$_2$F$_2$ | FEC | PS | ESA |
| Example 1 | additive I, 0.5 wt % | 1 | 3 | 0.5 | 0.5 |
| Comparative Example 1 | — | 1 | 3 | 0.5 | 0.5 |

The components listed in Table 1 are as follows.
Additive I: 3-(methylsulfonyl)-6-oxa-3-azabicyclo[3.1.0]hexane
LiPO$_2$F$_2$: lithium difluorophosphate
FEC: fluoro ethylene carbonate PS: 1,3-propane sultone
ESA: ethylene sulfate Experimental Example (1) Measurement of Capacity Retention (Ret) after High Temperature Storage The lithium secondary batteries of Example and Comparative Example were subjected to 0.5 C CC/CV charging (4.2V, 0.05 C CUT-OFF) and 0.5 C CC discharging (2.7V CUT-OFF) at 25° C. by three cycles, and a discharge capacity C1 at the 3rd cycle was measured.

After storing the charged lithium secondary battery at 60° C. for 16 weeks, the batteries were additionally maintained at room temperature for 30 minutes, and a discharge capacity C2 was measured by 0.5 C CC discharging (2.75V CUT-OFF). A capacity retention was calculated as follows. The results are shown in Table 2 below and FIG. 3.

Capacity Retention(%)=C2/C1×100(%)

(2) Measurement of Internal Resistance (DCIR) Increase Ratio after High Temperature Storage The lithium secondary battery of each Example and Comparative Example was 0.5 C CC/CV charged (4.2V 0.05 C CUT-OFF) at 25° C., and then 0.5 C CC discharged until a SOC 60%. At the SOC 60% point, DCIR R1 was measured by discharging for 10 seconds and complementary charging while changing the C-rate to 0.2 C, 0.5 C, 1 C, 1.5 C, 2 C and 2.5 C The charged lithium secondary battery was exposed to air at 60° C. for 16 weeks. The battery was further left at room temperature for 30 minutes, and then DCIR R2 was measured by the same method as described above. An internal resistance increase ratio was calculated as follows. The results are shown in Table 2 below and FIG. 4.

Internal resistance increase ratio (%)=(R2−R1)/R1×100(%)

(3) Measurement of Battery Thickness after High Temperature Storage

After charging the lithium secondary batteries of Example and Comparative Example at 25° C. under conditions of 0.5 C CC/CV (4.2V 0.05 C CUT-OFF), a battery thickness T1 was measured.

After exposing the charged lithium secondary batteries to air at 60° C. for 16 weeks (using a thermostat), a battery thickness T2 was measured. The battery thickness was measured using a plate thickness measuring device (Mitutoyo, 543-490B). A battery thickness increase ratio was calculated as follows. The results are shown in Table 2 below and FIG. 5.

Battery thickness increase ratio (%)=(T2−T1)/T1×100(%)

TABLE 2

|  | high temperature storage properties | | |
| --- | --- | --- | --- |
|  | Ret. (%) | DCIR increase ratio (%) | thickness increase ratio (%) |
| Example 1 | 74.9 | 156.0 | 123.4 |
| Comparative Example 1 | 73.2 | 169.6 | 136.9 |

Figure 3:
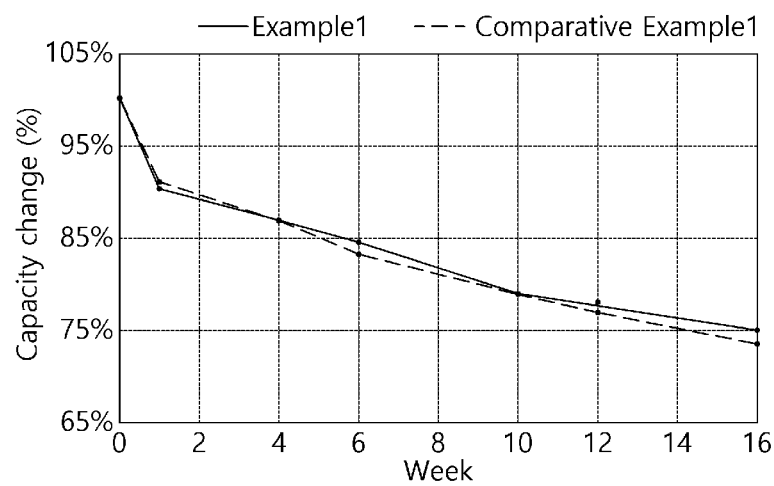
FIG. 3 is a graph showing capacity retentions of secondary batteries according to Example and Comparative Example under a high temperature (60° C.) condition.
Figure 4:
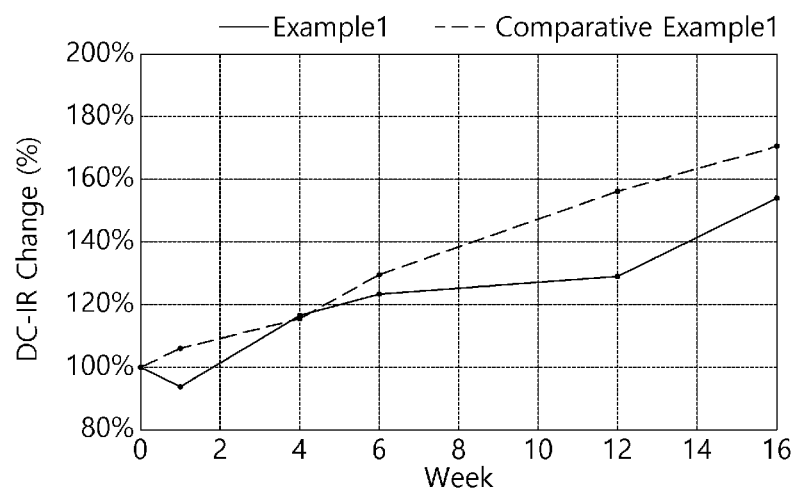
FIG. 4 is a graph showing resistance increase ratios of secondary batteries according to Example and Comparative Example under a high temperature (60° C.) condition.
Figure 5:
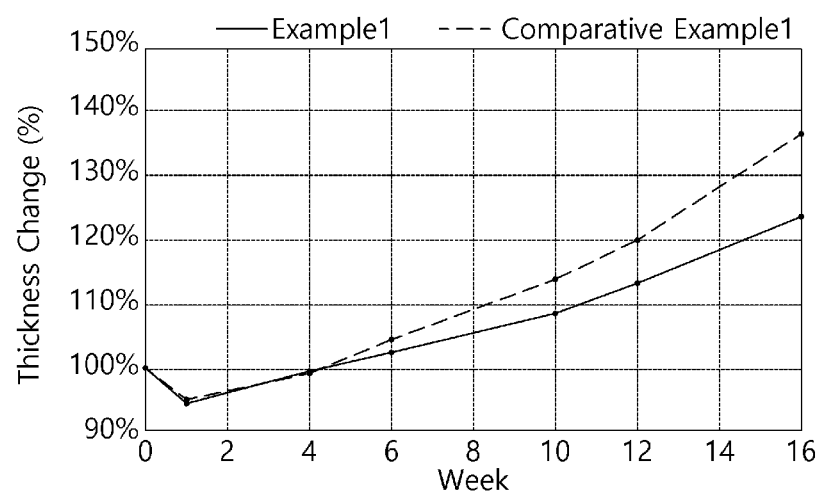
FIG. 5 is a graph showing thickness increase ratios of secondary batteries according to Example and Comparative Example under a high temperature (60° C.) condition.

Referring to Table 2 and FIGS. 3 to 5, the high-temperature storage performance (capacity retention, resistance increase ratio and thickness increase ratio) of the lithium secondary battery of Example 1 was improved.

What is claimed is:

1. An electrolyte solution for a lithium secondary battery, comprising:
   an additive comprising a compound represented by Chemical Formula 1;
   an organic solvent; and
   a lithium salt:

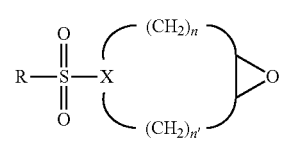

[Chemical Formula 1]

wherein, in Chemical Formula 1, R is hydrogen or a substituted or unsubstituted $C_1$-$C_5$ alkyl group, X is N or P, and n and n' are each independently an integer of 1 to 5.

2. The electrolyte solution for a lithium secondary battery of claim 1, wherein R is an unsubstituted $C_1$-$C_3$ alkyl group, and n and n' are each independently an integer of 1 to 3.

3. The electrolyte solution for a lithium secondary battery of claim 1, wherein R is an unsubstituted $C_1$ alkyl group, X is N, and n and n' are each 1.

4. The electrolyte solution for a lithium secondary battery of claim 1, wherein the additive is comprised in an amount ranging from 0.1 wt % to 5 wt % based on a total weight of the electrolyte solution.

5. The electrolyte solution for a lithium secondary battery of claim 1, wherein the additive is comprised in an amount ranging from 0.5 wt % to 2 wt % based on a total weight of the electrolyte solution.

6. The electrolyte solution for a lithium secondary battery of claim 1, wherein the organic solvent comprises at least one selected from the group consisting of a carbonate-based solvent, an ester-based solvent, an ether-based solvent, a ketone-based solvent, an alcohol-based solvent, an aprotic solvent, and mixtures thereof.

7. The electrolyte solution for a lithium secondary battery of claim 1, wherein the electrolyte solution further comprises an auxiliary additive comprising at least one selected from the group consisting of a cyclic carbonate-based compound, a fluorine-substituted carbonate-based compound, a sultone-based compound, a cyclic sulfate-based compound, a phosphate-based compound, and mixtures thereof.

8. The electrolyte solution for a lithium secondary battery of claim 7, wherein the auxiliary additive is comprised in an amount ranging from 0.05 wt % to 20 wt % based on a total weight of the electrolyte solution.

9. The electrolyte solution for a lithium secondary battery of claim 7, wherein the auxiliary additive is comprised in an amount ranging from 0.1 wt % to 15 wt % based on a total weight of the electrolyte solution.

10. A lithium secondary battery, comprising:
    an electrode assembly in which a plurality of cathodes and a plurality of anodes are repeatedly stacked;
    a case accommodating the electrode assembly; and
    the electrolyte solution for a lithium secondary battery of claim 1 accommodated together with the electrode assembly in the case.

11. A method for preparing a lithium secondary battery, comprising:

providing an electrode assembly in which a plurality of cathodes and a plurality of anodes are repeatedly stacked;

providing a case accommodating the electrode assembly; and providing an electrolyte solution for a lithium secondary battery, comprising:
an additive comprising a compound represented by Chemical Formula 1;
an organic solvent; and
a lithium salt:

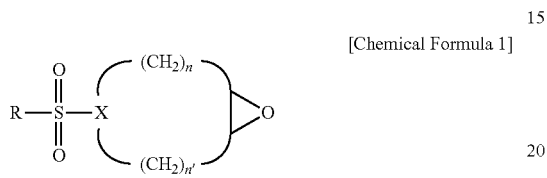

[Chemical Formula 1]

wherein, in Chemical Formula 1, R is hydrogen or a substituted or unsubstituted $C_1$-$C_5$ alkyl group, X is N or P, and n and n' are each independently an integer of 1 to 5, accommodated together with the electrode assembly in the case.

* * * * *